United States Patent
Vanderbur

(10) Patent No.: US 9,644,163 B2
(45) Date of Patent: May 9, 2017

(54) METHODS FOR MAKING AND DISTRIBUTING BATCHES OF BUTANE-ENRICHED GASOLINE

(71) Applicant: Sunoco Partners Marketing & Terminals L.P., Philadelphia, PA (US)

(72) Inventor: Steven M. Vanderbur, Houston, TX (US)

(73) Assignee: Sunoco Partners Marketing & Terminals L.P., Philadelphia, PA (US)

( * ) Notice: Subject to any disclaimer, the term of this patent is extended or adjusted under 35 U.S.C. 154(b) by 0 days.

(21) Appl. No.: 14/658,396

(22) Filed: Mar. 16, 2015

(65) Prior Publication Data

US 2015/0184102 A1     Jul. 2, 2015

Related U.S. Application Data

(62) Division of application No. 13/742,727, filed on Jan. 16, 2013, now Pat. No. 9,321,977.

(60) Provisional application No. 61/590,128, filed on Jan. 24, 2012.

(51) Int. Cl.
| | |
|---|---|
| C10L 10/14 | (2006.01) |
| G01N 33/28 | (2006.01) |
| C10L 1/04 | (2006.01) |
| C10L 1/06 | (2006.01) |
| C10L 1/16 | (2006.01) |
| G01L 7/00 | (2006.01) |
| G01N 33/22 | (2006.01) |

(52) U.S. Cl.
CPC .................. *C10L 10/14* (2013.01); *C10L 1/04* (2013.01); *C10L 1/06* (2013.01); *C10L 1/1608* (2013.01); *G01L 7/00* (2013.01); *G01N 33/22* (2013.01); *G01N 33/2829* (2013.01); *C10L 2200/0423* (2013.01); *C10L 2270/023* (2013.01); *C10L 2290/24* (2013.01)

(58) Field of Classification Search
CPC .. C10L 1/04; C10L 1/06; C10L 1/1608; C10L 10/14; C10L 2200/0423; C10L 2270/023; C10L 2290/24; G01L 7/00; G01N 33/22; G01N 33/28; G01N 33/2829
USPC ...... 222/25, 26, 71, 72; 141/9, 83, 104, 105, 141/192, 198; 137/486, 625.41
See application file for complete search history.

(56) References Cited

U.S. PATENT DOCUMENTS

| | | |
|---|---|---|
| 2,246,875 A | 6/1941 | Carney |
| 2,297,185 A | 9/1942 | Hollander et al. |
| 3,179,291 A | 4/1965 | Umbach et al. |

(Continued)

FOREIGN PATENT DOCUMENTS

| | | |
|---|---|---|
| CA | 2435113 | 1/2005 |
| WO | WO 2007-124058 | 11/2007 |

OTHER PUBLICATIONS

EPA Q & A Date Oct. 3, 1904, Abstract.

(Continued)

*Primary Examiner* — Timothy L Maust
*Assistant Examiner* — Andrew Schmid
(74) *Attorney, Agent, or Firm* — Clark Sullivan

(57) ABSTRACT

Disclosed are automated methods and systems for certifying the volatility of butane-enriched gasoline downstream of a butane blending operation. Such automated methods and systems provide significant advantages to comply with volatility requirements imposed by EPA or state regulations.

8 Claims, 5 Drawing Sheets

(56) References Cited

U.S. PATENT DOCUMENTS

| | | |
|---|---|---|
| 3,342,199 A | 9/1967 | McEvoy |
| 3,484,590 A | 12/1969 | Stanton |
| 3,751,644 A | 8/1973 | Mayer |
| 3,813,925 A | 6/1974 | Fenske et al. |
| 3,904,508 A | 9/1975 | Whyte et al. |
| 3,999,959 A | 12/1976 | Bajek |
| 4,268,701 A | 5/1981 | Dang Vu et al. |
| 4,523,928 A | 6/1985 | Hillman et al. |
| 4,543,819 A | 10/1985 | Chin et al. |
| 3,410,293 A | 11/1988 | Ernyei |
| 4,876,653 A | 10/1989 | McSpadden et al. |
| 4,882,041 A | 11/1989 | Scott |
| 5,004,850 A | 4/1991 | Wilson |
| 5,093,533 A | 3/1992 | Wilson |
| 5,133,391 A | 7/1992 | Johansson et al. |
| 5,163,586 A | 11/1992 | Zinsmeyer |
| 5,193,594 A | 3/1993 | Johansson et al. |
| 5,208,402 A | 5/1993 | Wilson |
| 5,271,526 A | 12/1993 | Williams |
| 5,344,044 A | 9/1994 | Hayden et al. |
| 5,423,607 A | 6/1995 | Jones et al. |
| 5,430,295 A | 7/1995 | Le Febre et al. |
| 5,542,450 A | 8/1996 | King et al. |
| 5,823,669 A | 10/1998 | Jones |
| 5,860,457 A | 1/1999 | Andersson |
| 5,975,353 A | 11/1999 | Finlayson |
| 5,979,705 A | 11/1999 | Kaehler et al. |
| 6,026,991 A | 2/2000 | Matthews |
| 6,109,286 A | 8/2000 | Johnston |
| 6,161,060 A | 12/2000 | Collins |
| 6,163,738 A | 12/2000 | Miller |
| 6,258,987 B1 | 7/2001 | Schmidt et al. |
| 6,328,772 B1 | 12/2001 | Scott |
| 6,679,302 B1 * | 1/2004 | Mattingly ............ G05D 11/131 137/486 |
| 7,032,629 B1 | 4/2006 | Mattingly et al. |
| 7,631,671 B2 | 12/2009 | Mattingly et al. |
| 8,176,951 B2 | 5/2012 | Mattingly et al. |
| 8,192,510 B2 | 6/2012 | Mattingly et al. |
| 2005/0022446 A1 | 2/2005 | Brundage et al. |
| 2005/0058016 A1 | 3/2005 | Smith et al. |
| 2006/0278304 A1 | 12/2006 | Mattingly et al. |
| 2007/0034550 A1 | 2/2007 | Hedrick |
| 2010/0175313 A1 * | 7/2010 | Mattingly ............... C10L 1/023 44/451 |
| 2012/0216453 A1 | 8/2012 | Mattingly et al. |

OTHER PUBLICATIONS

Grabner Instruments, "About Vapor Pressure Testing," from Grabner Instruments website, 2013.
Haskell, N.B. et al., Front-End Volatility of Gasoline Blend Industrial and Engineering Chemistry, vol. 34, No. 2, Feb. 1942, pp. 167-170.
Stewart, W,E., "Predict RVP of Blends Accurately," Petroleum Refiner, vol. 38, No. 6, Jun. 1959, pp. 231-234.
Standard Test Method for Vapor Pressure of Petroleum Products (Reid Method); from Organic website (http//organic.ulsan.ac.kr/reid.html), 2013.
Vazquez-Esparragoza, J. et el., "How to Estimate Reid Vapor Pressure (RVP) of Blends," Bryan Research &Engineering, Inc., website, Encyclopedia of Chemical Processing and Design, vol. 47, pp. 415-424; Hydrocarbon Processing, Aug. 1992, pp. 135-138.
Compliance Monitoring for Vapor Pressure or Vapor-Liquid Ratio Temperature, MiniVap On-line Petrolab Company website, 2013.
Spectro, "Sulfur Monitors and Analyzers for Fuels and Oils," from Spectro website, 2013.
Sindie, "Sindie On-line Analyzer," from Sindie website, 2013.
Environmental Protection Agency, "Gasoline Blending Regulations," 40 G.F.R. § 80.27, 80.41, 80.46, 80,65, 80, 195, 80.340.
Reynolds, Robert E., "The Current Fuel Ethanol Industry Transportation, Marketing, Distribution, and Technical Considerations," Downstream Alternatives Inc., May 15, 2000.
Monder, Dayadeep S., Real-Time Optimization of Gasoline Blending with Uncertain Parameters, University of Alberta, Spring 2001.
International Search Report and Written Opinion issued Mar. 5, 2010 in International Patent Application No. PCT/EP10/20207.
International Search Report and Written Opinion, dated May 2, 2014, which issued during the prosecution of International Patent Application No. PCT/US2013/038761, which corresponds to the present application.
International Search Report and Written Opinion, dated Jun. 10, 2014, which issued during the prosecution of International Patent Application No. PCT/US2013/069447, which corresponds to the present application.

* cited by examiner

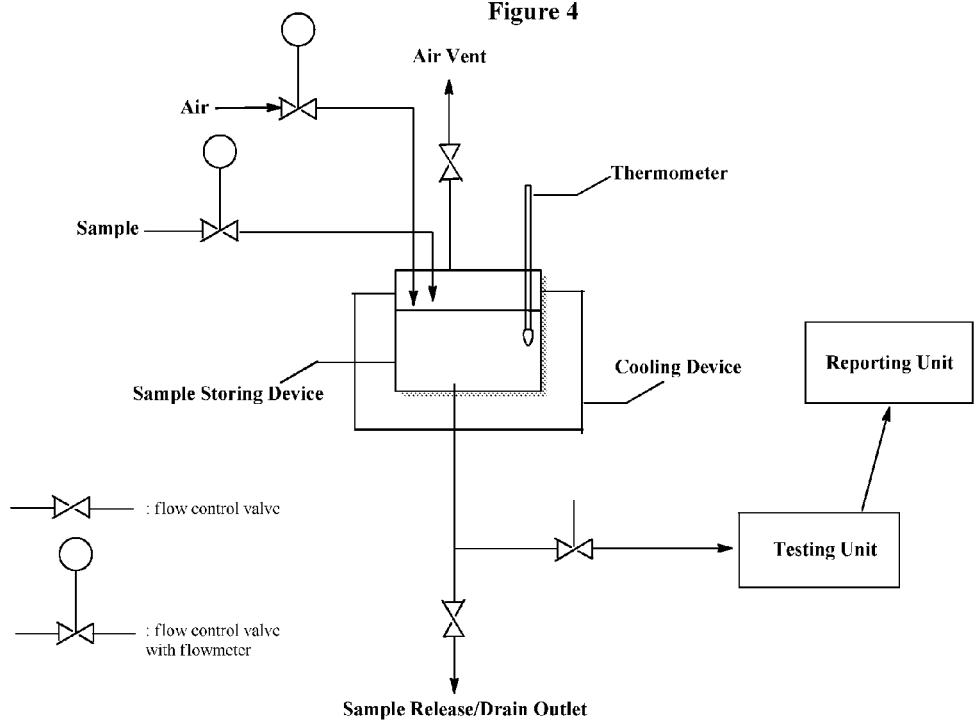

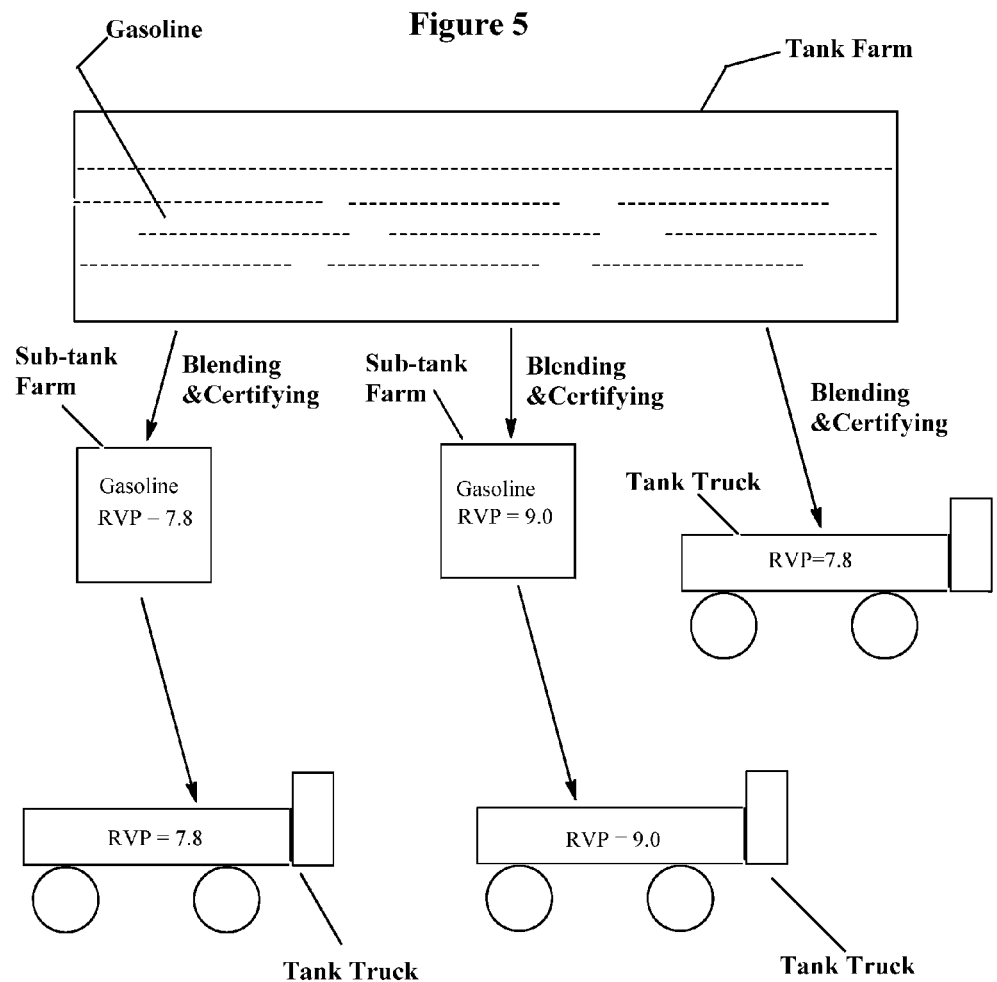

METHODS FOR MAKING AND DISTRIBUTING BATCHES OF BUTANE-ENRICHED GASOLINE

CROSS-REFERENCE TO RELATED APPLICATIONS

The present application is a divisional of U.S. application Ser. No. 13/742,727 filed Jan. 16, 2013, which claims the benefit of U.S. Provisional Application No. 61/590,128 filed Jan. 24, 2012. The disclosures of these application is incorporated by reference.

FIELD OF THE INVENTION

Background of the Invention

A significant physical property of gasoline is its volatility, or its ability to combust. There are two physical properties that are primarily used to measure the volatility of gasoline: (1) vapor pressure, and (2) vapor-liquid ratio. The Reid method is the standard test for measuring the vapor pressure of petroleum products. Reid vapor pressure is related to true vapor pressure, but is a more accurate assessment for petroleum products because it considers sample vaporization as well as the presence of water vapor and air in the measuring chamber.

In order to keep cars performing at a consistent level year-round, gasoline marketers blend volatility-modifying agents such as butane with gasoline to increase the volatility of the gasoline, especially during the colder months. The addition of butane also reduces the cost of the gasoline, since the unit cost of butane is typically less than the unit cost of gasoline. Butane can be added to the gasoline supply at several points along the gasoline distribution chain. The first opportunity to blend butane with gasoline is at the refinery, according to processes like those disclosed in Mayer, U.S. Pat. No. 3,751,644. This patent, which is owned by Sun Oil Company, describes a system for automatically adjusting the amount of butane added to a gasoline stream at a petroleum refinery based on continuous measurements of the Reid vapor pressure of the gasoline downstream from the point of blending. This downstream feedback control system adjusts the amount of butane added to the gasoline based on measurements taken downstream of the blending operation, and does not include measuring the volatility upstream of the blending operation, or calculating the blend ratio based on the upstream volatility.

Bajek's U.S. Pat. No. 3,999,959, which is owned by Universal Oil Products Company, also discloses a system for blending butane and gasoline at a petroleum refinery. The Bajek system blends butane with a low-octane gasoline stream and a high-octane gasoline stream, and then analyzes the blended gasoline to measure characteristics such as Reid vapor pressure and vapor to liquid ratio. Bajek does not disclose monitoring the gasoline upstream of the blending operation, or calculating the blend ratio based upon such upstream monitoring.

Butane is also added to gasoline while it is transported in the pipeline, after consolidation of various trunk lines from refineries. The inventors are aware of an unpatented system that is used to blend butane and gasoline at several terminal tank farms. These systems continuously monitor the Reid vapor pressure of gasoline that is introduced to a storage tank, and blend butane with the gasoline based upon the vapor pressure measurements. The butane is supplied by a tanker truck, as opposed to a permanent on-site mounted butane bullet. These unpatented systems do not automatically vary the blending process based upon the time of year, petroleum destination, or type of gasoline, but instead require manual oversight and control of the process. These unpatented systems also do not continuously monitor the Reid vapor pressure downstream of the blending operation as an integrity check. Instead, they certify the integrity of the blending operation by periodically measuring the Reid vapor pressure of the entire storage tank.

The third point of blending is at the tank farm, e.g., when gasoline is delivered to a large storage tank, the volatility of the tank is measured, and sufficient butane is added to the tank to attain a desired volatility. Butane can also be added immediately before the gasoline is dispensed to a tanker truck at the rack, or before gasoline is loaded onto a ship. Methods of blending butane into various gasoline streams are described by the present inventors in U.S. Pat. Nos. 6,679,302 and 7,631,671.

Because gasoline vapor emissions are a major component of volatile organic compounds (VOC's) in the atmosphere, the United States Environmental Protection Agency (EPA) has promulgated regulations that govern the maximum volatility of gasoline based on geographic regions in the United States during particular times of year. These regulations generally apply from May 1 through September 15, when the gasoline is warmest and most volatile, and require that any blended gasoline be certified for compliance with the volatility guidelines. See 40 C.F.R. §80.27. EPA has also promulgated regulations that prescribe the methods for testing blended gasoline for volatility. In particular, these regulations require that volatility be determined using American Society for Testing and Materials (ASTM) standard test method ASTM D5191. See 40 C.F.R. §§80.82 and 80.46.

Existing methods of enriching gasoline with butane generally monitor volatility upstream of the blending operation, determine the ratio that gasoline and butane can be blended together to achieve a desired vapor pressure, and blend the gasoline and butane at the blend ratio. Although these methods and systems are precise, they are inadequate for making batches of butane-enriched gasoline, especially during the summer months, because of the need to certify the volatility of the batch after production using manual testing techniques. Further, the existing methods and systems suffer from a substantial lack of automation, and methods of tailoring the blending operation to produce batches that meet the particular volatility requirements of a geographic region during any given time of the year.

SUMMARY OF THE INVENTION

The present invention solves the foregoing problems by, for the first time, providing a fully integrated method for distributing butane-enriched gasoline batches that includes automated methods for blending those batches to pre-defined volatility limits, and certifying the volatility of those batches using sophisticated automated methods that achieve relevant levels of statistical significance. The invention further provides automated methods and devices for certifying compliance with such volatility limits, and automated methods of blending butane with gasoline in batches to meet individualized volatility requirements of particular geographic regions.

In a first principal embodiment the invention provides an automated method of making a batch of butane-enriched gasoline within a very narrow volatility range, while simultaneously certifying the volatility of the batch with a high degree of probability.

The remarkable blending accuracy achieved by the invention, the consistency observed among batches, and the accuracy of the batch certification process, are accomplished through a novel sequence of steps comprising:

a) prescribing a maximum volatility for a given batch;
b) providing a flow of gasoline through a conduit, wherein said gasoline has a volatility and a flow rate, and said flow has a start time and an end time corresponding to the batch of gasoline (the "batch interval");
c) withdrawing a sample of said gasoline through a first withdrawal port on said conduit and measuring the volatility of said sample;
d) calculating a ratio at which butane can be blended with said gasoline to produce a blended gasoline having a volatility less than or equal to the maximum volatility;
e) blending butane through an automated blending unit into said gasoline stream downstream of said first withdrawal port at a blend rate that is based on said ratio calculated in step (d) and the flow rate of gasoline through said conduit, thereby producing butane-enriched gasoline;
f) continually repeating steps (c) and (d) on an automated basis at prescribed intervals throughout the batch interval, and adjusting the blend rate in step (e) based upon changes to the ratio calculated in step (d);
g) certifying the volatility of the batch by:
  i) withdrawing a sample of said butane-enriched gasoline through a second withdrawal port on said conduit;
  ii) chilling said sample to approximately zero or one degree Celsius;
  iii) saturating said sample with air;
  iv) measuring the volatility of said sample; and
  v) recording in a database the volatility measured in sub-step (iv); and
h) repeating step (g) on an automated basis at prescribed intervals throughout the batch interval.

In a preferred embodiment, the batch is simultaneously discharged to a transport vehicle such as a tanker truck, cargo ship, rail car or barge while the batch is being generated. Moreover, the volatility measured in step (g) is preferably reported in a database in comparison to the maximum volatility initially prescribed for the batch, to complete the certification process. In another embodiment, there is a 95% probability or greater that the volatility of the batch is less than the prescribed volatility limit, but within 5% of the prescribed volatility limit.

In another embodiment, the invention provides a method of making custom batches of butane-enriched gasoline at a butane blending facility that meet volatility limits imposed on particular geographic regions. In this particular embodiment, the method comprises the following steps:

a) providing a plurality of volatility limits in a database, wherein each of said volatility limits is associated with one or more geographic access codes;
b) receiving a geographic access code at one or more information processing units and accessing the associated volatility limit in said database;
c) providing a flow of gasoline through a conduit, wherein said gasoline has a volatility and a flow rate, and said flow has a start time and an end time corresponding to a batch of gasoline (the "batch interval");
d) withdrawing a sample of said gasoline through a first withdrawal port on said conduit and measuring the volatility of said sample;
e) based on the volatility limit accessed in step (b), and the volatility measured in step (d), calculating through said one or more information processing units a maximum ratio at which butane can be blended with said gasoline to produce gasoline having a volatility less than or equal to the volatility limit;
f) blending butane through an automated blending unit into said gasoline stream downstream of said first withdrawal port at a blend rate that is based on said ratio calculated in step (e) and the flow rate of gasoline through said conduit;
g) continually repeating steps (d) and (e) on an automated basis at prescribed intervals throughout the batch interval, and adjusting the blend rate in step (f) based upon changes to the ratio calculated in step (e);
h) dispensing said gasoline from step (f) into one or more gasoline transport vehicles;
i) receiving a second geographic access code at said one or more information processing units, and accessing the associated volatility limit in said database for said second geographic access code;
j) providing a second start time and a second end time for said flow corresponding to a second batch of gasoline (the "second batch interval"); and
k) repeating steps (d) through (h) during said second batch interval based upon said second geographic access code.

In a particularly preferred embodiment, the geographic access code is received at the information processing unit based upon data entered at a rack, immediately prior to producing the batch and filling a tanker truck with the batch. Thus, for example, the driver of a truck that pulls up to a rack for loading might enter the zip code(s) of the locations to where the gasoline will be delivered, and such zip code(s) will be used as or translated to a geographic codes that determines the relevant associated maximum volatility level. Alternatively, the destination of the load might be pre-registered at the facility and associated with a particular shipment code. When the driver pulls up to the rack he inputs a pre-set shipment code, and the information process unit receives the geographic access code by accessing the registered shipment information.

In yet another embodiment, the invention provides an automated method and device, which can be integrated into an automated butane-enrichment system, for periodically analyzing samples of butane-enriched gasoline for their volatility. In this embodiment, which produces test results having an accuracy of greater than 95%, the method comprises:

a) blending butane through an automated blending unit into a flow of gasoline to produce butane-enriched gasoline, wherein said flow is defined by a start time and an end time corresponding to a batch of gasoline (the "batch interval");
b) providing means for automatically measuring the volatility of gasoline by withdrawing a sample of gasoline from the gasoline flow; chilling the sample to approximately zero or one degree Celsius; saturating said sample with air; and measuring the volatility of said sample;
c) implementing said means to measure the volatility of the gasoline produced in step (a); and
d) recording in a database the volatility measured in step (c).

In still another embodiment the invention provides methods for tracking and evaluating key performance indicators of a butane blending operation, such as lost blending opportunities arising from a system shut-down or interruption in butane supply. By correlating these events with actual pipeline information, such as fuel type and volatility, or blending parameters such as allowable volatility, geographic location or time of year, one is able to present a clear picture of the efficiency of the operation and its cost savings. Thus, in still another embodiment the invention provides a method of evaluating key performance indicators in a butane blending system comprising:

a) providing a central information processing unit that maintains hourly time;
b) providing a petroleum conduit and a flow of petroleum through said conduit;
c) providing a butane supply and a butane blending system on said petroleum conduit;
d) detecting points in time when said butane blending system stops and resumes operation; and
e) associating said points in time with said hourly time, and generating data corresponding to segments of hourly time when said butane blending system stopped and resumed operation during a given time frame ("inoperative time segments").

The methods of the invention offer a number of advantages over prior art systems and methods, including but not limited to the following:

The vapor pressure in the butane-enriched gasoline is more thoroughly controlled and accurately defined, thus greatly improving the process of complying with vapor pressure requirements imposed by state and federal regulators;

Gasoline distribution facilities are able to increase the efficiency of their butane blending operations and the utilization of butane in those operations; and Gasoline distribution facilities are able to ensure compliance with vapor pressure limits imposed in specific geographic regions, and to adapt their operations to maximize butane use in specific geographic regions.

These and other objects, features, and advantages of the present invention may be more clearly understood and appreciated from a review of the following detailed description of the disclosed embodiments and by reference to the appended drawings and claims.

DESCRIPTION OF THE FIGURES

FIG. 4 is a schematic view of an automated device capable of certifying the vapor pressure of butane-enriched gasoline.

FIG. 5 is a schematic view of an automated system for certifying the vapor pressure of gasoline downstream of a butane blending operation at a tank farm, a sub-tank farm or a tanker truck.

DETAILED DESCRIPTION OF THE INVENTION

Definitions and Methods of Measurement

Figure 1:
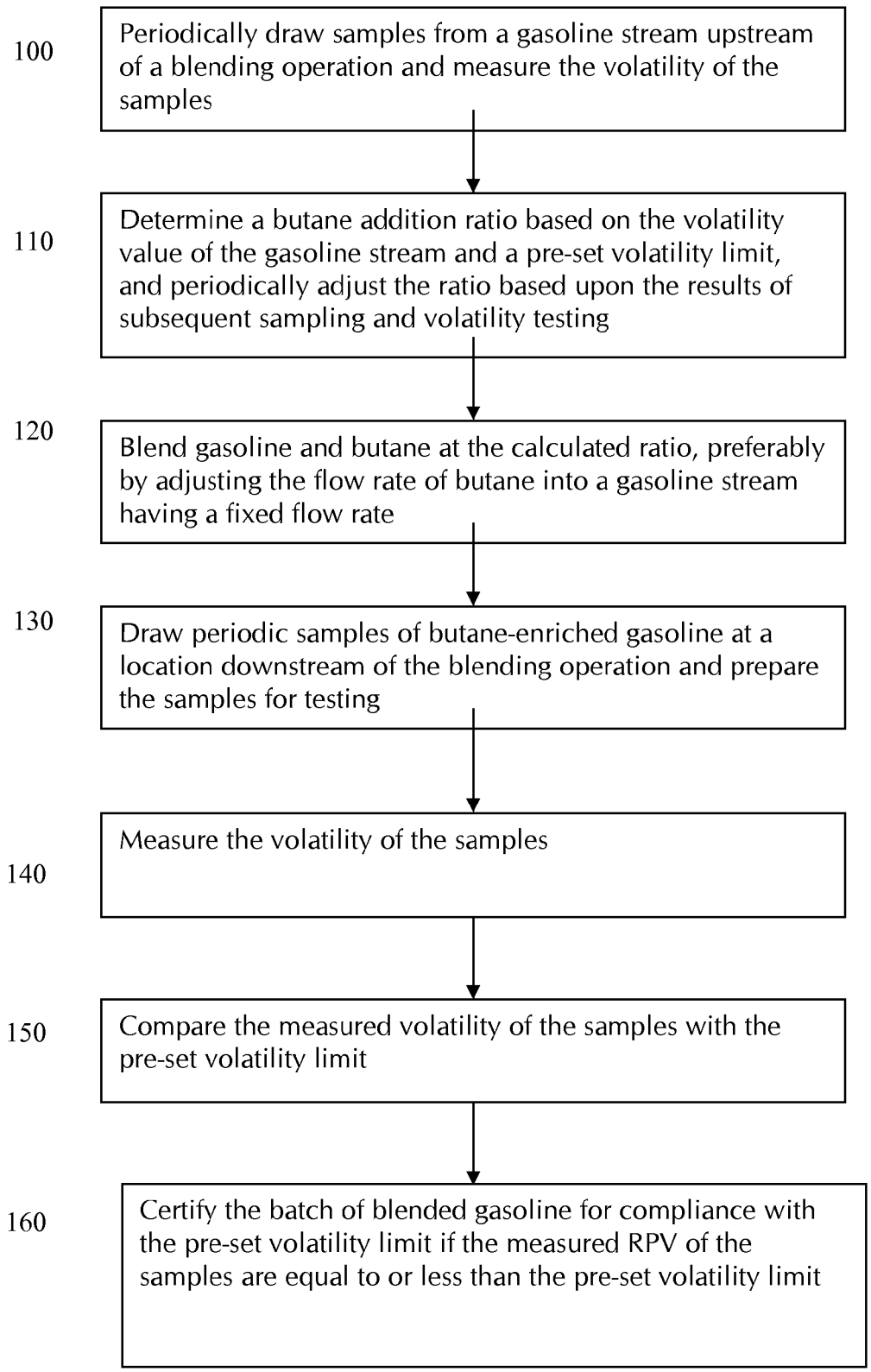
FIG. 1 is a logic flow diagram of an exemplary process of blending butane into a gasoline stream to a predetermined vapor pressure, and for certifying the vapor pressure of the butane-enriched gasoline.

Throughout this patent application, whenever an analysis of gasoline or butane is disclosed, the analysis is to be performed in accordance with applicable EPA regulations and American Society for Testing and Materials ("ASTM") methods in force as of the date of this application. Therefore, the following ASTM methods are to be used when applicable:

The term "volatility" is used herein to refer to the capacity of a liquid to vaporize, and can be measured by any suitable physical property, including vapor pressure or distillation temperature.

When vapor pressure is measured according to the present invention, it will be understood that any suitable measure of vapor pressure could be taken, including Reid vapor pressure and/or vapor/liquid ratio. For measuring the Reid vapor pressure of reformulated gasoline, ASTM standard method D 5191-01, entitled "Standard Test Method for Vapor Pressure of Petroleum Products (Mini Method)" can be used. The following correlation can also be used to satisfy EPA regulations:

$$\text{volatility}_{EPA}=(0.956*\text{volatility}_{ASTM})-2.39 \text{ kPa}$$

For measuring the temperature at which a given percentage of gasoline is volatilized, ASTM standard D 86-01, should be used. This method measures the percentage of a gasoline sample that evaporates as a function of temperature as the sample is heated under controlled conditions. $T_D$ refers to the temperature at which a given percentage of gasoline volatilizes using ASTM standard D 86-01 as the test method, T(50) refers to the temperature at which 50% of gasoline volatilizes using ASTM standard D 86-01 as the test method, etc.

In another embodiment, the volatility measuring device detects total vapor pressure or absolute vapor pressure (AVP) of said sample. The total vapor pressure is converted to corresponding dry vapor pressure equivalent (DVPE) according to the following equation:

$$\text{DVPE (in kPa)}=(0.956\times\text{total vapor pressure (in kPa)})-2.39 \text{ kPa}.$$

AVP refers to the pressure of the air-free sample and is calculated from the total vapor pressure of the sample by subtracting out the partial pressure of the dissolved air. Total vapor pressure refers to the observed pressure measured by the testing unit that is the sum of the partial pressure of the sample and the partial pressure of the dissolved air.

The term gasoline, when used herein, refers to any refined petroleum product that flows through a petroleum pipeline. The term also includes any liquid that can be used as fuel in an internal combustion engine, non-limiting examples of which include fuels with an octane rating between 80 and 95, fuels with an octane rating between 80 and 85, fuels with an octane rating between 85 and 90, and fuels with an octane rating between 90 and 95. The term includes products that consist mostly of aliphatic components, as well as products that contain aromatic components and branched hydrocarbons such as iso-octane. The term also includes all grades of conventional gasoline, reformulated gasoline ("RFG"), diesel fuel, biodiesel fuel, jet fuel, and transmix. The term also includes blendstock for oxygenate blending ("BOB"), which is typically used for blending with ethanol. BOBs include RBOB (reformulated gasoline blendstock), PBOB (premium gasoline blendstock), CBOB (conventional gasoline blendstock), subgrade gasoline, and any other blendstock used for oxygenate or ethanol blending.

The term "gasoline supply," when used herein, refers to a source of gasoline from any storage tank or any point along a petroleum pipeline. The term includes gasoline from the line between a storage tank and the rack, gasoline from a pipeline that transmits multiple types of gasoline, and gasoline from a pipeline that transmits only one type of gasoline.

A continuous flow of gasoline should be contrasted with a flow of gasoline in a rack blending operation, which occurs in intervals (i.e. start and stop periods), and in increments (i.e. where the flow rate depends on the capacity of a single pumping system, and is proportionate to the number of tankers being filled by a single pump at any one time.) It will be understood that a continuous flow can be interrupted for brief periods of time, for maintenance and other pipeline related activities.

The term "fixed," when used herein, refers to a previously determined value for a physical property of a blend. For example, when it is stated that butane-enriched gasoline has fixed volatility, it is understood that it has been previously determined that the blend will have the volatility. Likewise, when it is stated that a ratio of butane is calculated that can be blended into a sample without causing the sample to pass a fixed volatility limit, it is understood that it has been previously determined that the sample mixed with the butane at the ratio will make a blend that meets the limit.

The term "certifying" refers to the process of recording one or more measured values from a flow of gasoline, and reporting such measured values in a format that permits comparison to a pre-defined limit. The value measured for purposes of certification is typically not used for feedback control of a given process.

The term "information processing unit," when used herein, refers to a data processing system which can receive, retrieve, store, process, and output data. The information processing unit processes data which has been captured and encoded in a format recognizable by the data processing system. The information processing unit communicates with other information processing unit(s), information database(s), component(s), system(s) and device(s) encompassed by the methods and systems of the present invention.

The term "informational database," when used herein, refers to a data storing system which can receive, store and output data. The informational database communicates with other informational database(s), information processing unit(s), component(s), system(s) and device(s) encompassed by the methods and systems of the present invention.

Discussion

In a first primary embodiment the invention provides an automated method of making a batch of butane-enriched gasoline and simultaneously certifying the volatility of the batch, comprising: (a) providing a maximum volatility for the batch; (b) providing a flow of gasoline through a conduit, wherein said gasoline has a volatility and a flow rate, and said flow has a start time and an end time corresponding to the batch of gasoline (the "batch interval"); (c) withdrawing a sample of said gasoline through a first withdrawal port on said conduit and measuring the volatility of said sample; (d) calculating a ratio at which butane can be blended with said gasoline to produce a blended gasoline having a volatility less than or equal to the maximum volatility; (e) blending butane through an automated blending unit into said gasoline stream downstream of said first withdrawal port at a blend rate that is based on said ratio calculated in step (d) and the flow rate of gasoline through said conduit, thereby producing butane-enriched gasoline; (f) continually repeating steps (c) and (d) on an automated basis at prescribed intervals throughout the batch interval, and adjusting the blend rate in step (e) based upon changes to the ratio calculated in step (d); (g) measuring the volatility of the butane-enriched gasoline by: (i) withdrawing a sample of said butane-enriched gasoline through a second withdrawal port on said conduit; (ii) chilling said sample to approximately zero or one degree Celsius; (iii) saturating said sample with air; (iv) measuring the volatility of said sample; and (v) recording in a database the volatility measured in sub-step (iv); and (h) continually repeating step (g) on an automated basis at prescribed intervals throughout the batch interval.

In a second principal embodiment the invention provides an automated method of distributing a plurality of batches of gasoline having different volatility limits, said method comprising: (a) providing a plurality of volatility limits in a database, wherein each of said volatility limits is associated with a distinct geographic access code; (b) receiving a geographic access code at one or more information processing units and accessing the associated volatility limit in said database; (c) providing a flow of gasoline through a conduit, wherein said gasoline has a volatility and a flow rate, and said flow has a start time and an end time corresponding to a batch of gasoline (the "batch interval"); (d) withdrawing a sample of said gasoline through a first withdrawal port on said conduit and measuring the volatility of said sample; (e) based on the volatility limit accessed in step (b), and the volatility measured in step (d), calculating through said one or more information processing units a maximum ratio at which butane can be blended with said gasoline to produce gasoline having a volatility less than or equal to the volatility limit; (f) blending butane through an automated blending unit into said gasoline stream downstream of said first withdrawal port at a blend rate that is based on said ratio calculated in step (e) and the flow rate of gasoline through said conduit; (g) continually repeating steps (d) and (e) on an automated basis at prescribed intervals throughout the batch interval, and adjusting the blend rate in step (f) based upon changes to the ratio calculated in step (e); (h) dispensing said gasoline from step (f) into one or more gasoline transport vehicles; (i) receiving a second geographic access code at said one or more information processing units, and accessing the associated volatility limit in said database for said second geographic access code; (j) providing a second start time and a second end time for said flow corresponding to a second batch of gasoline (the "second batch interval"); and (k) repeating steps (d) through (h) during said second batch interval based upon said second geographic access code.

In yet another principal embodiment, the invention provides an automated method of making a batch of butane-enriched gasoline and simultaneously certifying the volatility of the batch comprising: (a) blending butane through an automated blending unit into a flow of gasoline to produce said butane-enriched gasoline, wherein said flow is defined by a start time and an end time corresponding to a batch of gasoline (the "batch interval"); (b) providing means for automatically measuring the volatility of gasoline by withdrawing a sample of gasoline from a gasoline flow; chilling said sample to approximately zero or one degree Celsius; saturating said sample with air; and measuring the volatility of said sample; (c) implementing said means to measure the volatility of the gasoline produced in step (a); and (d) recording in a database the volatility measured in step (c).

In still another principal embodiment the invention provides methods of monitoring the operational efficiency of a butane blending operation, particularly by identifying and quantifying lost blending opportunities based on when the blending system might not be working. The method can be used to determine when the supply of butane at a facility is depleted and, by keeping track of the flow of gasoline and the potential blending opportunity, the lost butane blending opportunity can be calculated and quantified. Thus, in another embodiment, the invention provides an automated method of generating key performance indicators of a butane blending operation comprising:

a) providing a central information processing unit that maintains hourly time;

b) providing a petroleum conduit and a flow of petroleum through said conduit;

c) providing a butane supply and a butane blending system on said petroleum conduit;

d) detecting points in time when said butane blending system stops and resumes operation;

e) associating said points in time with said hourly time, and generating data corresponding to segments of hourly time when said butane blending system stopped and resumed operation during a given time frame ("inoperative time segments").

The invention also provides systems and methods based on any combination of the foregoing principal embodiments. The invention supports numerous sub-embodiments. Unless otherwise stated, each of the sub-embodiments and operational features discussed below can be applied equally to each of the principal embodiments. In like manner, the invention provides both methods of blending and the system components for blending, and it will be understood that each method embodiment has a corresponding system embodiment, and that each system embodiment has a corresponding method embodiment.

Furthermore, unless otherwise specified, each of the following embodiments can be implemented at any point along a petroleum pipeline—i.e. at the rack, where gasoline is unloaded onto transport tanker trucks ("at the rack" includes both (1) along the line from a storage tank immediately prior to the rack and (2) along the line between a storage tank and an intermediate temporary storage tank immediately prior to the rack), along a consolidated pipeline that transmits multiple types of gasoline from different sources such as refineries or ports, and along a pipeline that transmits only one type of gasoline (as in a line that transmits only one type of gasoline to an above-ground storage tank). The tank farm from which the butane-enriched batches of gasoline are distributed may be a terminal gasoline tank farm (where tanker trucks are filled), an intermediate gasoline tank farm (from which gasoline is distributed to multiple end locations), or a combined use tank farm (that serves as an intermediate point and a terminal point). In one embodiment, the systems and methods further include transmitting the blended gasoline stream to an above-ground storage tank (i.e. a tank that is permanently constructed on a piece of land, typically with berms around its periphery to contain any petroleum spills) or an intermediate temporary storage tank immediately prior to the rack.

It will be understood that the invention can be practiced with any type of gasoline with which butane can permissibly be blended, including conventional gasoline, reformulated gasoline, and BOB. It will also be understood that the methods can be practiced with volatility modifying agents other than butane, and that each of the embodiments expressed herein can be practiced equally using such other agents. In like manner, it will be understood that the volatility can be measured using any measure of volatility, including vapor pressure, vapor-liquid ratio and distillation temperature.

By sampling the gasoline upstream of the butane blending operation at predetermined intervals, and periodically re-adjusting the butane blend ratio according to the volatility of each sample, it is possible to accurately reach specific volatility levels in the final batch. By sampling the gasoline at predetermined intervals a second time, after butane has been blended into the gasoline to produce the butane-enriched gasoline, and measuring the volatility of the samples using the particular methods of the present invention, it is possible to certify that an entire batch of butane enriched gasoline does not exceed its pre-defined volatility limit. This is accomplished by recording in a consolidated location all of the volatility test results from the certification process, and either confirming that none of the results exceed the pre-defined upper limit on volatility, or averaging the results based on the gasoline flow rate observed at the time of measurement to confirm that the average volatility does not exceed the pre-defined upper limit.

Numerous methods exist for calculating the ratio of butane that can be blended with a mixture of a given volatility. U.S. Pat. Nos. 7,032,629 and 6,679,302, PCT Patent Application No. WO 2007/124058, and U.S. Patent Application No. 2006/0278304, the contents of which are hereby incorporated by reference, describe such methods of calculation. The blend ratio of butane to gasoline required to attain the fixed volatility can be determined simply by direct volumetric averaging of the volatility of the butane and ethanol-blended gasoline. However, it has been noted in the literature that volumetric averaging can yield low estimates of resultant volatility, especially when the amount of butane added is less than 25%. Methods for determining blend ratios to attain a prescribed volatility which overcome these observed limitations on volumetric averaging are set forth more fully in "How to Estimate Reid Vapor Pressure (volatility) of Blends," J. Vazquez-Esparragoza, Hydrocarbon Processing, August 1992; and "Predict volatility of Blends Accurately," W. E. Stewart, Petroleum Refiner, June 1959; and "Front-End Volatility of Gasoline Blends," N. B. Haskell et al., Industrial and Engineering Chemistry, February 1942, the disclosure from each being hereby incorporated by reference as if fully set forth herein.

In a particular embodiment, the analyzing unit can generate a volatility signal based on the volatility, and the information processing unit ("IPU") can receive the volatility signal and calculate the ratio of butane based upon the volatility derived from the volatility signal. Furthermore, the IPU can generate a blending signal based on the ratio of butane; and the blending unit can receive the blending signal and blend the butane, ethanol, and gasoline based upon the signal from the IPU.

The methods and systems of the present invention can employ data and programming that takes into account regulatory limits on volatility based on the time of year and geographical region, and automatically vary the blend ratio based on those limits. In a particular embodiment, the method can further comprise storing, in one or more informational databases, seasonal data that prescribes the fixed volatility requirement on two or more prescribed dates or ranges of dates; and calculating the ratio of butane based upon current date information and the seasonal data. Likewise, in a particular embodiment, the system can further comprise one or more informational databases storing seasonal data that prescribes the fixed volatility requirement on two or more prescribed dates or ranges of dates. The IPU can receive this seasonal data, and calculate the ratio of butane based upon current date information and the seasonal data.

The volatility is preferably measured as a vapor pressure, a vapor liquid ratio, a distillation temperature requirement, or combinations thereof. The vapor pressure requirement can comprise a maximum allowable vapor pressure, a minimum allowable vapor pressure, a maximum allowable vapor liquid ratio, a minimum allowable vapor liquid ratio, or a minimum allowable distillation temperature. In particular embodiments, the minimum allowable distillation temperature can comprise a minimum T(50), a minimum T(10), or both a minimum T(50) and a minimum T(10).

In a particular embodiment, the volatility measurement comprises a vapor pressure measurement and a distillation temperature measurement, and the volatility requirement comprises a maximum allowable vapor pressure and a minimum allowable distillation temperature. The ratio of butane can then be calculated so that the final blend meets both the maximum allowable vapor pressure and the minimum allowable distillation temperature.

In a particular embodiment, the volatility can be measured by an analyzing unit that includes an analyzer such as a Grabner unit or a Bartec Distillation Process Analyzer (DPA). For example, the analyzing unit can include a Grabner unit for obtaining vapor pressure and vapor liquid ratio measurements, and a Bartec unit for obtaining distillation temperature measurements. In particular embodiments, a Grabner unit can be used to obtain volatility measurements on a periodic basis of about 3 to about 5 times per hour, and a Bartec unit can used to obtain volatility measurements on a periodic basis of about 2 times per hour.

The testing unit typically comprises a testing chamber, a pressure measuring device, a vacuum pump and a thermostatically controlling device. In one embodiment, the testing chamber has a suitable capacity of from about 5 ml to about 50 ml of liquid and vapor and can maintain a vapor-to-liquid ratio of from 3.95:1.00 to 4.05:1.00. In another embodiment, the testing chamber is evacuated and/or cleaned prior to sample introduction. In still another embodiment, the pressure measuring device and/or the thermostatically controlling device is periodically calibrated prior to testing. In another embodiment, the testing chamber is maintained at a suitable temperature during the duration of volatility measurement by said thermostatically controlling device, for example, a representative example of the suitable temperature is about 37.8±0.1° C. Non-limiting examples of thermostatically controlling devices include cooling/heating baths, ovens, refrigerators and equivalents. In one embodiment, measuring volatility of the gasoline sample is performed after said sample reaches thermal equilibrium at a suitable temperature in the testing chamber.

Regarding the testing unit, the vacuum pump is connected to the testing chamber and is operable to reduce the pressure of said testing chamber to less than 0.01 kPa absolute. With respect to the pressure measuring device, it is connected to the testing chamber and is preferably operable to measure the vapor pressure of said sample. The pressure measuring device can measure local station pressure with an accuracy of 0.2 kPa or better. In one embodiment, the pressure measuring device comprises one or more pressure transducers. The pressure transducer has a minimum operational range of from 0 to 177 kPa with a minimum resolution of 0.1 kPa and a minimum accuracy of ±0.8 kPa. The pressure transducer is periodically calibrated prior to testing, for example, at least every six months. Regarding the calibration, the pressure transducer is calibrated using two reference points: zero pressure (<0.1 lPa) and the ambient barometric pressure.

In one optional embodiment, a flow meter is integrated into the gasoline conduit, and used to calculate the butane addition rate necessary to achieve the calculated blend ratio. In another embodiment, the flow occurs at a substantially fixed rate, and the fixed rate is programmed into the logic used to calculate the butane addition rate. In another embodiment, the overall flow of the system remains the same over time, but the flow rate used in the calculation must be adjusted when, for example, more than one batch is being produced at one time. Thus, for example, when a single pump with a fixed displacement is used at a rack, and two batches are produced at once, the flow rate for each batch will be ½ the rate if only one batch were produced. If the flow rate is programmed into the logic, the method will also include detecting the number of batches being produced, and reducing the flow rate of each batch used to calculate the butane addition rate proportionately, and logic for accomplishing such steps.

Any of the foregoing data, including the fixed volatility requirements, volatility measurements, flow rates, and rate or ratio of butane blending, can be stored in a database accessible to a remote location through a dedicated or Internet connection. Furthermore, any of the data or signals encoding the data can be transmitted via dedicated or internet connections between the components of the system.

In a particular embodiment, the sampling, measuring and blending steps and systems are located in close proximity to one another. For example, the sampling, measuring and blending systems can be housed on a discreet, permanently mounted skid or platform. Alternatively, the sampling, measuring and blending steps and systems are located in different locations. For example, the sampling and measuring steps can occur at any location upstream of the blending.

The valves that control the flow of butane into the gasoline, under the direction of the IPU at the calculated blend rate and blend ratio, are critical components of the systems. The blending unit preferably employs two valves—(1) an on/off valve located between the gasoline stream and the butane stream, that prevents gasoline from entering the blending unit, and which can be completely shut off when blending is not permitted, and (2) a modulating (a/k/a control) valve that controls the flow of butane towards or from the first valve. The second valve controls the butane flow rate by modulating the size of the flow orifice and the pressure of the butane stream downstream of the valve. The valves may also be under the control of one or more remote information processing units, as described in greater detail elsewhere in this document.

The systems and methods also provide real time information regarding the butane supply used for the blending operation, and IPU access to the butane supply information, optionally through a remote Internet connection. The butane is preferably supplied to the blending unit from one or more butane storage units known as bullets that can contain in excess of 1,000, 10,000 or even 100,000 gallons of butane. These bullets are typically mounted on the same site as the blending operation, but sufficiently remote from the blending unit that extensive piping is used to transmit the butane either above or below ground. In a preferred embodiment, information about the supply of butane storage and transmission process is continuously taken, stored and used to ensure the integrity and safety of the butane supply and blending operations. For example, pressure sensors will typically be installed on the butane piping at the butane supply and at the blending operation (before and after the butane traverses a facility to the blending operation), so that the pressures can be compared to ensure no leaks in the underground piping. The pressure information derived from these sensors is preferably reconciled and reported in user-friendly format by an IPU. A temperature gauge may also be installed on the butane storage unit, again accessible by the IPU which transmits and displays the temperatures to the operator of the blending operation.

It will be understood that there is some variability in the vapor pressure of commercial supplies of butane. As a result, the vapor pressure of the butane stream may be periodically measured, and the blend ratio and blend rate should be based on the vapor pressure of the butane. The butane vapor pressure may be measured at the same frequency as the gasoline, but is typically measured at a lesser frequency than the gasoline vapor pressure, often on the order of 1, 2, 3 or 4 times per day. In addition, the butane vapor pressure can be measured at the butane storage unit, before the butane travels underground to the blending operation, rather than on the same skid as the blending operation.

The systems and methods of the invention also preferably employ one or more information processing units (IPUs) that control the blending process, and that record and report the results of the blending and monitoring processes. The IPUs may thus store or have access to numerous types of information used in the blending process, including:

- Allowable vapor pressures based on the destination of the gasoline and the time of year (typically stored on an IPU controlled by the butane blender);
- Allowable distillation temperatures based on the destination of the gasoline and the time of year (typically stored on an IPU controlled by the butane blender);
- Whether blending is permitted based upon the time of year or the destination of the batch (typically stored on the blender's IPU);
- Whether blending is permitted, based upon the type of gasoline in a batch (typically stored on an IPU controlled by the blender);
- Current date and time information (typically stored and varied on an IPU controlled by the butane blender);
- The flow rate of gasoline passing the blending operation (typically generated as pulses by a flow meter controlled by the pipeline operator, and accessed by the blender's IPU);
- Batch data such as the type of gasoline in the batch, the volume of gasoline in the batch, and/or the destination of the batch (typically provided as information or batch codes stored on an IPU controlled by the pipeline operator, and accessed by (i.e. received or retrieved by) the blender's IPU); and/or
- Start and end times or points for a batch (often stored on an IPU controlled by the pipeline operator when performing blending on continuous streams of gasoline, and accessed by the blender's IPU; when creating individual batches for tanker trucks, such data will typically be generated based on the actual blending operation).

In operation, the blender's IPUs will access the corresponding date, petroleum type, and/or destination of the gasoline stream, and calculate the blend ratio and/or blend rate based upon the allowable vapor pressure for the retrieved seasonal data, date, petroleum type and/or destination for the gasoline stream. Alternatively or in addition, the IPU may access a listing of petroleum products for which blending with butane is impermissible, and dictate a zero blend rate or blend ratio based upon the gasoline type in a particular batch that is passing the blending unit.

In addition, the IPUs control numerous physical operations of the blending process, including the valves, the upstream and downstream vapor pressure monitoring processes, the upstream and downstream distillation temperature monitoring processes, and the butane sampling process. The one or more IPUs are thus logically programmed to execute one or more of the following physical processes:

- Modulate the on/off valve depending on whether blending is permitted;
- Modulate the orifice of the second valve to accomplish the desired blending rate and ratio;
- Withdraw and return gasoline from the petroleum pipeline at a predetermined frequency for vapor pressure and/or TD measurements; and/or
- Withdraw snippets of butane into a reservoir at a predetermined frequency.

After performing various blending and monitoring functions, the blender's IPU will typically generate and consolidate data that describes the results of the blending process, correlates blending data with batch information supplied by the pipeline operator, and validates the integrity and safety of the entire blending process, including:

- Vapor pressure and/or TD of gasoline upstream of the blending unit at particular times;
- Vapor pressure and/or TD of gasoline downstream of the blending unit at particular times;
- Settings for daily calibration of the gasoline vapor pressure sensor(s);
- The date(s) of blending covered by the dataset;
- Batch start and end times;
- The quantity of butane blended into a gasoline batch (i.e. the quantity of gasoline created in the batch);
- The type of gasoline in a batch;
- Batch destination;
- Butane quantity stored in any butane storage units, given by date and time;
- Vapor pressure of butane at prescribed sampling times;
- Sulfur content of butane blended into the gasoline;
- Metered volumes of butane withdrawn from any butane storage units for defined periods of time;
- Volumes of butane blended into the gasoline stream, calculated from butane blend rates, for defined periods of time;
- The pressure of butane at two or more points between the butane storage unit and the butane blending unit; and
- The temperature of any butane storage tank that supply butane to the blending unit.

In one embodiment, this information is used to generate reports of lost butane blending opportunities, which might arise when, for example, the butane supply at the facility is depleted, the valves on the blending unit are inoperable, or some other malfunction. The presence of a central timing unit that can be used to track petroleum batches flowing through the conduit is an important aspect of this embodiment because, by correlating the time with key attributes of the batches over time, one is able to correlate the lost blending opportunity to the key attribute, and thereby calculate the value of the lost blending opportunity. Key attributes of the flow that will affect the lost opportunity include the volatility of the petroleum, which can be measured according to methods described elsewhere herein, the flow rate of the petroleum, which can be monitored by an information processing unit associated with the butane blending unit or a central information processing unit maintained by the facility, and the type of petroleum flowing through the pipeline, which will typically be derived from batch codes stored on a central information processing unit maintained at the facility, and received from an upstream source that has added the batch into the pipeline.

This information can be retrieved, stored and generated in report formats as required by the butane blender or pipeline operator. In addition, all of this data is preferably accessible at a remote location through a suitably programmed information processing unit.

Any of the foregoing data may be stored in a database accessible to a remote location through a dedicated or Internet connection. In a preferred embodiment, gasoline creation data (i.e. butane consumption data) will preferably be accessed by an IPU controlled by the pipeline operator, which will update the volume of any batch passing through the pipeline based on the butane addition.

The gasoline stream of the foregoing embodiments may have a gasoline flow rate that does not vary over time, and therefore, the blend rate can be calculated based upon a preset gasoline flow rate. As used throughout this application, the term "flow rate" refers to a volume of a fluid that flows past a given point over a given period of time. Alternatively, the gasoline stream may have a gasoline flow rate that varies within a batch of gasoline, and therefore, utilization of the invention will further comprise periodically determining the gasoline flow rate through the pipeline, and periodically recalculating the butane blend rate based upon the gasoline flow rate and a calculated blend ratio. Specifically, any of the foregoing embodiments blending gasoline with constant or variable flow rates may further comprise one or more information processing units in informational communication with said upstream vapor pressure sensors, logically programmed to calculate a calculated blend ratio and calculated blend rate based upon the vapor pressure and volumetric flow rate of said gasoline stream, and for communicating said calculated blend ratio and calculated blend rate to said blending unit; wherein said blending unit periodically receives said calculated blend ratio and calculated blend rate from said one or more IPUs, and adjusts the actual blend ratio and actual blend rate to coincide with said calculated blend ratio and calculated blend rate.

Additionally, the systems of the foregoing embodiments may further comprise a butane sampling unit for periodically or continuously withdrawing butane from said butane stream. Said butane sampling units may be under the control of one or more information processing units, wherein said one or more information processing units may cause said butane sampling unit to withdraw into a reservoir at least one sample of butane from said butane stream at least every 500,000 gallons of butane. Said reservoir may be manually withdrawn periodically from said butane sampling unit, and any butane contained in said reservoir may be tested for sulfur content.

FIG. 1 illustrates an exemplary process of producing butane-enriched gasoline and certifying the volatility of the butane enriched gasoline downstream of a butane blending operation. In FIG. 1, the process begins with step 100, which includes drawing periodic samples from a gasoline stream upstream of a butane blending operation and checking the volatility of the samples. Subsequently, in step 110, a butane blend ratio is calculated based on the measured volatility and pre-set volatility. Then in step 120 the gasoline and butane are blended according to the calculated butane blend ratio. Once the blending of gasoline and butane is complete, in step 130, a sample of butane-enriched gasoline is withdrawn at a location downstream of the blending operation and prepared for testing. In step 140, the volatility of the sample is measured and then, in step 150, the measured volatility of the sample is compared with the pre-set volatility limit. Finally, in step 160, the blended gasoline stream is certified if the measured volatility does not exceed the pre-set volatility limit.

Figure 2:
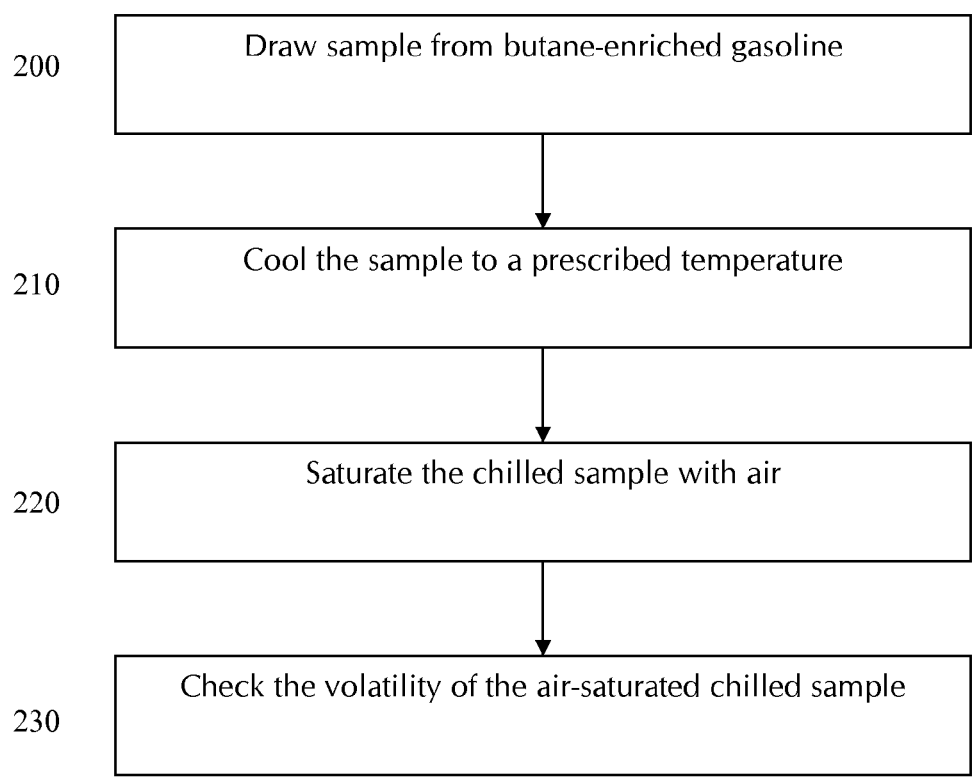
FIG. 2 is a logic flow diagram of an automated process for certifying the vapor pressure of butane-enriched gasoline.

FIG. 2 is an illustration of a process of the certifying the volatility of butane-enriched gasoline downstream of a butane blending operation in accordance with the present invention. In step 200, a sample of butane-enriched gasoline is withdrawn at a location downstream of the blending operation. The sample is subsequently cooled to a designated temperature in step 210 (preferably from about 0 to about 1° C.) and then saturated with air in step 220. The volatility of the chilled air-saturated sample is then measured in step 230.

Figure 3:
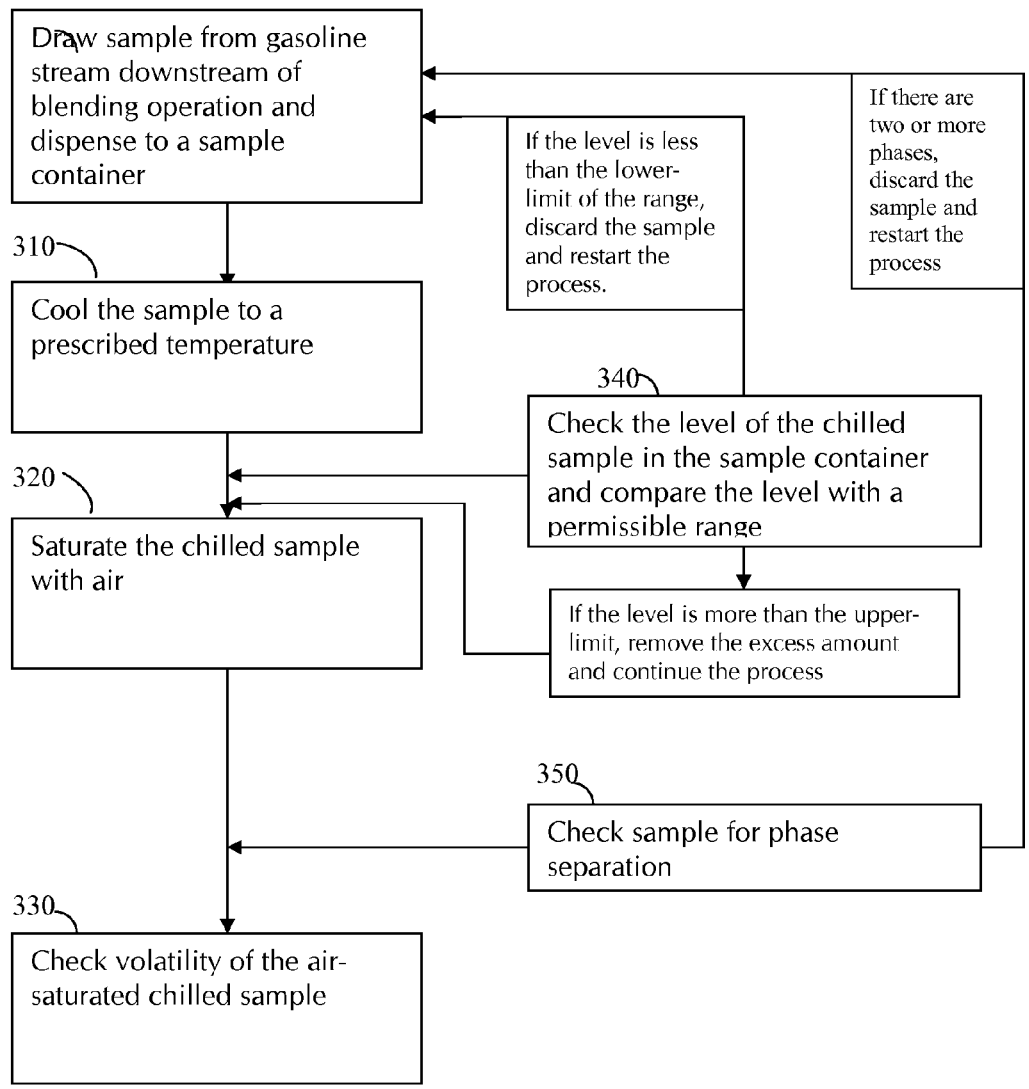
FIG. 3 is a logic flow diagram illustrating an automated process for certifying the vapor pressure of butane-enriched gasoline, incorporating automated processes for chilling and aerating the sample.

FIG. 3 illustrates a process of certifying the volatility of butane-enriched gasoline downstream of a butane blending operation taking into account limits on the sample volume, and further accounting for the potential for phase separation in the sample. The difference between FIG. 3 and FIG. 2 is the addition of steps 340 and 350, while steps 200, 210, 220 and 230 of FIG. 2 are identical to steps 300, 310, 320 and 330 of FIG. 3 respectively. Although the size of the sample container can vary to a large extent, the container typically has a capacity of from 250 ml to 1 L.

After the sample from step 310 has been has been chilled, the level of the chilled sample in the sample container is preferably checked. If the filling level is less than the lower-limit of a pre-determined range, typically 70-80% of the total container volume, the sample is discarded and the process is returned to step 300 for re-sampling. Alternatively, if the filling level is more than the upper-limit of the pre-determined desired range, the excess sample is removed from the container and the process advances to step 320, where the chilled sample if saturated with air.

Once a chilled air-saturated sample is obtained in step 320, step 350 may check for phase separation and, if there are two or more phases in the sample, the sample is discarded and the process is returned to step 300. If the sample exists as a single phase, the process moves to step 330, and the volatility of the sample is measured.

FIG. 4 is a schematic diagram of an automated device for certifying the volatility of gasoline downstream of a butane blending operation. A sample of a gasoline stream is first withdrawn from a conduit and delivered to a sample storing device, e.g., a sample container. The sample storing device is cooled by a cooling device, which cools the sample to a designated temperature. The cooling device can be any means which provides sufficient and effective cooling, for example, a cooling jacket where one or more cooling agents are circulated in the cooling jacket; or a refrigerator. A thermometer is inserted in the sample storing device to detect the sample temperature and the result is communicated to the cooling device directly or indirectly through process control units that control the operation of the cooling device by, for example, adjusting the circulation volume and rate of the cooling agents in the cooling jacket, or adjusting the refrigerator's power switch. Air is delivered into the sample storing device to facilitate the air-saturation of the sample stored in the sample storing device. Air-saturation of the sample can be achieved by various means, for example, the inlet hose/pipe of the air can be inserted under the surface level of the sample, and bubbling air through the sample to achieve sufficient air-saturation of the sample; or the air can be delivered over the surface level of the sample and the sample storing device shaken until the sample is saturated with air. The air outlet is operated to release or vent excess air. The sample release or drain outlet is operated to drain part of the sample if there is sample overflow in the sample storing device, or to withdraw the sample and deliver to the testing unit, or otherwise drain the sample out of the sample storing device. The testing unit analyzes the sample and generates an output which can be transmitted to a reporting unit whereupon a report of the test results can be generated.

FIG. 5 is an illustration of an automated system for certifying the volatility of gasoline downstream of a butane blending operation at the location of a tank farm or a tank truck. The gasoline from the tank farm can be blended with butane according to the most stringent geographic and time of year restrictions, pumped to the tanker truck and delivered to the designated location. Alternatively, the gasoline from the tank farm can be blended with butane according to different local volatility requirements, pumped to different sub-tank farms with designated volatility, and be delivered to tanker trucks to corresponding specific locations.

EXAMPLE

The following iterative procedure described in "How to Estimate Reid Vapor Pressure (volatility) of Blends," J. Vazquez-Esparragoza, Hydrocarbon Processing, August 1992, can be used to predict the volatility of a mixture of hydrocarbon components. Importantly, the procedure can be used for hydrocarbon components defined by either their chemical composition or their physical properties. For this reason, it can be used to calculate the volatility of a blend of (1) butane, which has a known chemical composition, and (2) a mixture of gasoline and ethanol, which has an unknown chemical composition, but can be defined by its physical properties obtained from a volatility analysis. Advantageously, the algorithm can by implemented in a computer simulation.

Step 1. Calculate the molecular weight (MW) of the sample mixture:

$$MW_{mix} = \Sigma_i x_i MW_i$$

Step 2. Evaluate the density ($\rho$) of the sample at T=35, 60, and 100° F. Compute the liquid expansion of the sample using n=4:

$$V_o = \rho_{60}((n+1)/\rho_{35} - 1/\rho_{100})$$

Step 3. Make a flash calculation at 100° F. For the first calculation, assume an initial ratio of the equilibrium liquid L and feed liquid F so that L/F=0.97.

Step 4. Using the values from step 3, calculate a new L/F with the equation:

$$L/F = 1/(1 + (\rho_V MW_L / \rho_L MW_V (V_o/(\rho_V/\rho_{LF}))))$$

Step 5. Use the value of L/F from step 4 to recalculate the flash from step 3 and a new value of L/F from step 4. In most cases, the assumed and calculated values agree within the specified criterion within less than five iterations.

Step 6. The volatility is the flash pressure for the value of L/F obtained by iteration.

Throughout this application, various publications are referenced. The disclosures of these publications are hereby incorporated by reference in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An automated method of distributing a plurality of batches of gasoline having different volatility limits, said method comprising:
  a) providing a plurality of volatility limits in a database, wherein each of said volatility limits is associated with a distinct geographic access code;
  b) receiving a geographic access code at one or more information processing units and accessing the associated volatility limit in said database;
  c) providing a flow of gasoline through a conduit, wherein said gasoline has a volatility and a flow rate, and said flow has a start time and an end time corresponding to a batch of gasoline (the "batch interval");
  d) withdrawing a sample of said gasoline through a first withdrawal port on said conduit and measuring the volatility of said sample;
  e) based on the volatility limit accessed in step (b), and the volatility measured in step (d), calculating through said one or more information processing units a maximum ratio at which butane can be blended with said gasoline to produce gasoline having a volatility less than or equal to the volatility limit;
  f) blending butane through an automated blending unit into said gasoline stream downstream of said first withdrawal port at a blend rate that is based on said ratio calculated in step (e) and the flow rate of gasoline through said conduit;
  g) continually repeating steps (d) and (e) on an automated basis at prescribed intervals throughout the batch interval, and adjusting the blend rate in step (f) based upon changes to the ratio calculated in step (e);
  h) dispensing said gasoline from step (f) into one or more gasoline transport vehicles;
  i) receiving a second geographic access code at said one or more information processing units, and accessing the associated volatility limit in said database for said second geographic access code;
  j) providing a second start time and a second end time for said flow corresponding to a second batch of gasoline (the "second batch interval"); and
  k) repeating steps (d) through (h) during said second batch interval based upon said second geographic access code, wherein said gasoline transport vehicles are tanker trucks, and said code communicated to said database in step (b) is a geographic code based on data entered by an operator of said tanker truck.

2. The method of claim 1, wherein said access codes are associated with one or more variables selected from geographical region and time of year.

3. The method of claim 1, wherein said access codes are associated with geographical region and time of year.

4. The method of claim 1 wherein:
  a) said gasoline transport vehicles are tanker trucks,
  b) said one or more codes communicated to said database in step (b) comprises a geographic code based on data entered by an operator of said tanker truck,
  c) said one or more codes communicated to said database in step (b) further comprises a date code automatically generated based on the current date.

5. An automated method of distributing a plurality of batches of gasoline having different volatility limits, said method comprising:
  a) providing a plurality of volatility limits in a database, wherein each of said volatility limits is associated with a distinct geographic access code;
  b) receiving a geographic access code at one or more information processing units and accessing the associated volatility limit in said database;
  c) providing a flow of gasoline through a conduit, wherein said gasoline has a volatility and a flow rate, and said flow has a start time and an end time corresponding to a batch of gasoline (the "batch interval");
  d) withdrawing a sample of said gasoline through a first withdrawal port on said conduit and measuring the volatility of said sample;
  e) based on the volatility limit accessed in step (b), and the volatility measured in step (d), calculating through said one or more information processing units a maximum ratio at which volatility modifying agent can be blended with said gasoline to produce gasoline having a volatility less than or equal to the volatility limit;
  f) blending volatility modifying agent through an automated blending unit into said gasoline stream downstream of said first withdrawal port at a blend rate that is based on said ratio calculated in step (e) and the flow rate of gasoline through said conduit;
  g) continually repeating steps (d) and (e) on an automated basis at prescribed intervals throughout the batch interval, and adjusting the blend rate in step (f) based upon changes to the ratio calculated in step (e);
  h) dispensing said gasoline from step (f) into one or more gasoline transport vehicles;
  i) receiving a second geographic access code at said one or more information processing units, and accessing the associated volatility limit in said database for said second geographic access code;
  j) providing a second start time and a second end time for said flow corresponding to a second batch of gasoline (the "second batch interval"); and
  k) repeating steps (d) through (h) during said second batch interval based upon said second geographic access code,
wherein said gasoline transport vehicles are tanker trucks, and said code communicated to said database in step (b) is a geographic code based on data entered by an operator of said tanker truck.

6. The method of claim 5, wherein said access codes are associated with one or more variables selected from geographical region and time of year.

7. The method of claim 5, wherein said access codes are associated with geographical region and time of year.

8. The method of claim 5 wherein:
  a) said gasoline transport vehicles are tanker trucks,
  b) said one or more codes communicated to said database in step (b) comprises a geographic code based on data entered by an operator of said tanker truck,
  c) said one or more codes communicated to said database in step (b) further comprises a date code automatically generated based on the current date.

* * * * *